(12) United States Patent
Mattes et al.

(10) Patent No.: US 8,172,760 B2
(45) Date of Patent: May 8, 2012

(54) MEDICAL DEVICE ENCAPSULATED WITHIN BONDED DIES

(75) Inventors: Michael F. Mattes, Chandler, AZ (US);
Paul F. Gerrish, Phoenix, AZ (US);
Anna J. Malin, Mesa, AZ (US); Tyler J. Mueller, Phoenix, AZ (US); Geoffrey DeWitt Batchelder, Chandler, AZ (US);
Clark B. Norgaard, Phoenix, AZ (US);
Michael A. Schugt, St. Paul, MN (US);
Ralph Danzl, Tempe, AZ (US); Richard J. O'Brien, Hugo, MN (US)

(73) Assignee: Medtronic, Inc., Minneapolis, MN (US)

( * ) Notice: Subject to any disclaimer, the term of this patent is extended or adjusted under 35 U.S.C. 154(b) by 377 days.

(21) Appl. No.: 12/487,369

(22) Filed: Jun. 18, 2009

(65) Prior Publication Data
US 2010/0324614 A1    Dec. 23, 2010

(51) Int. Cl.
*A61N 1/00* (2006.01)
(52) U.S. Cl. ...................................... 600/485
(58) Field of Classification Search ............... 607/23; 600/535, 505, 485
See application file for complete search history.

(56) References Cited

U.S. PATENT DOCUMENTS

| | | |
|---|---|---|
| 3,388,301 A | 6/1968 | James |
| 3,943,557 A | 3/1976 | Frazee et al. |
| 4,224,565 A | 9/1980 | Sosniak et al. |
| 4,285,002 A | 8/1981 | Campbell |
| 4,530,029 A | 7/1985 | Beristain |
| 4,684,884 A | 8/1987 | Soderlund |
| 4,701,826 A | 10/1987 | Mikkor |
| 4,773,972 A | 9/1988 | Mikkor |
| 4,775,831 A | 10/1988 | Annamalai |
| 4,868,712 A | 9/1989 | Woodman |
| 4,870,224 A | 9/1989 | Smith et al. |
| 5,059,899 A | 10/1991 | Farnworth et al. |
| 5,315,486 A | 5/1994 | Fillion et al. |
| 5,381,039 A | 1/1995 | Morrison |

(Continued)

FOREIGN PATENT DOCUMENTS

EP    1 128 174 A2    8/2001

OTHER PUBLICATIONS (PCT/US2010/039137) PCT Notification of Transmittal of the International Search Report and the Written Opinion of the International Searching Authority.

(Continued)

*Primary Examiner* — Scott Getzow
(74) *Attorney, Agent, or Firm* — Stephen W. Bauer; Carol F. Barry

(57) ABSTRACT

An implantable medical system includes a first die substrate with a first outer surface. The system also includes a second die substrate with a second outer surface. Furthermore, the system includes a medical device with a first portion that is mounted to the first die substrate and a second portion that is mounted to the second die substrate. The first and second die substrates are fixed to each other and substantially hermetically sealed to each other. Also, the medical device is substantially encapsulated between the first and second die substrates. The first portion is electrically connected to the second portion. Moreover, the first and second outer surfaces of the first and second die substrates are directly exposed to a biological material.

23 Claims, 4 Drawing Sheets

U.S. PATENT DOCUMENTS

| | | | |
|---|---|---|---|
| 5,381,804 | A | 1/1995 | Shambroom |
| 5,572,065 | A | 11/1996 | Burns |
| 5,592,391 | A | 1/1997 | Muyshondt et al. |
| 5,606,264 | A | 2/1997 | Licari et al. |
| 5,682,065 | A | 10/1997 | Farnworth et al. |
| 5,938,956 | A | 8/1999 | Hembree et al. |
| 5,955,789 | A | 9/1999 | Vendramin |
| 6,022,787 | A | 2/2000 | Ma |
| 6,032,064 | A | 2/2000 | Devlin et al. |
| 6,074,891 | A | 6/2000 | Staller |
| 6,144,866 | A | 11/2000 | Miesel et al. |
| 6,145,384 | A | 11/2000 | Ikeda et al. |
| 6,171,252 | B1 | 1/2001 | Roberts |
| 6,221,024 | B1 | 4/2001 | Miesel |
| 6,278,379 | B1 | 8/2001 | Allen et al. |
| 6,287,256 | B1 | 9/2001 | Park et al. |
| 6,297,072 | B1 | 10/2001 | Tilmans et al. |
| 6,297,551 | B1 | 10/2001 | Dudderar et al. |
| 6,298,255 | B1 | 10/2001 | Cordero et al. |
| 6,303,977 | B1 | 10/2001 | Schroen et al. |
| 6,323,550 | B1 | 11/2001 | Martin et al. |
| 6,394,953 | B1 | 5/2002 | Devlin et al. |
| 6,486,534 | B1 | 11/2002 | Sridharan et al. |
| 6,500,694 | B1 | 12/2002 | Enquist |
| 6,514,798 | B2 | 2/2003 | Farnworth |
| 6,515,870 | B1 | 2/2003 | Skinner et al. |
| 6,516,808 | B2 | 2/2003 | Schulman |
| 6,555,856 | B1 | 4/2003 | Staller |
| 6,563,133 | B1 | 5/2003 | Tong |
| 6,566,596 | B1 | 5/2003 | Askew |
| 6,566,736 | B1 | 5/2003 | Ogawa et al. |
| 6,638,784 | B2 | 10/2003 | Bartlett et al. |
| 6,696,369 | B2 | 2/2004 | Fraser et al. |
| 6,718,206 | B2 | 4/2004 | Casavant |
| 6,774,327 | B1 | 8/2004 | Wong |
| 6,821,342 | B2 | 11/2004 | Mattes et al. |
| 6,822,326 | B2 | 11/2004 | Enquist et al. |
| 6,855,115 | B2 | 2/2005 | Fonseca et al. |
| 6,867,073 | B1 | 3/2005 | Enquist |
| 6,874,367 | B2 | 4/2005 | Jakobsen et al. |
| 6,902,987 | B1 | 6/2005 | Tong et al. |
| 6,903,918 | B1 | 6/2005 | Brennan |
| 6,962,835 | B2 | 11/2005 | Tong et al. |
| 6,968,743 | B2 | 11/2005 | Rich et al. |
| 7,041,178 | B2 * | 5/2006 | Tong et al. .............. 148/33.4 |
| 7,096,580 | B2 | 8/2006 | Gonzalez et al. |
| 7,109,092 | B2 | 9/2006 | Tong |
| 7,126,212 | B2 | 10/2006 | Enquist et al. |
| 7,147,604 | B1 | 12/2006 | Allen et al. |
| 7,150,195 | B2 | 12/2006 | Jacobsen et al. |
| 7,162,926 | B1 | 1/2007 | Guziak et al. |
| 7,205,181 | B1 | 4/2007 | MacIntyre |
| 7,233,048 | B2 | 6/2007 | Rybnicek |
| 7,238,999 | B2 | 7/2007 | LaFond et al. |
| 7,247,517 | B2 | 7/2007 | Rumer et al. |
| 7,305,889 | B2 | 12/2007 | Fortin et al. |
| 7,318,264 | B2 | 1/2008 | Schugt |
| 7,396,698 | B2 | 7/2008 | Horning et al. |
| 7,403,818 | B2 | 7/2008 | Kramer et al. |
| 7,462,552 | B2 | 12/2008 | Tong et al. |
| 7,485,968 | B2 | 2/2009 | Enquist et al. |
| 7,495,462 | B2 | 2/2009 | Hua et al. |
| 7,540,188 | B2 | 6/2009 | Wiese et al. |
| 7,563,692 | B2 | 7/2009 | Fortin et al. |
| 7,622,324 | B2 | 11/2009 | Enquist et al. |
| 7,647,836 | B2 | 1/2010 | O'Brien et al. |
| 7,748,277 | B2 | 7/2010 | O'Brien et al. |
| 7,759,774 | B2 | 7/2010 | Fraser et al. |
| 7,781,250 | B2 | 8/2010 | Wang et al. |
| 7,829,363 | B2 | 11/2010 | You |
| 7,886,608 | B2 | 2/2011 | Mothilal et al. |
| 7,902,851 | B2 | 3/2011 | Fenner et al. |
| 8,072,056 | B2 | 12/2011 | Mueller et al. |
| 2001/0033024 | A1 | 10/2001 | Fraser et al. |
| 2002/0115920 | A1 | 8/2002 | Rich et al. |
| 2004/0079277 | A1 | 4/2004 | Mattes et al. |
| 2004/0186396 | A1 | 9/2004 | Roy et al. |
| 2004/0222478 | A1 | 11/2004 | Zhang et al. |
| 2005/0009246 | A1 | 1/2005 | Enquist et al. |
| 2005/0065565 | A1 | 3/2005 | Kramer et al. |
| 2006/0033204 | A1 | 2/2006 | Fraser et al. |
| 2006/0110854 | A1 | 5/2006 | Horning et al. |
| 2006/0264004 | A1 | 11/2006 | Tong et al. |
| 2006/0273430 | A1 | 12/2006 | Hua et al. |
| 2007/0037379 | A1 | 2/2007 | Enquist et al. |
| 2007/0107524 | A1 | 5/2007 | O'Brien |
| 2007/0158769 | A1 | 7/2007 | You |
| 2007/0179545 | A1 * | 8/2007 | Warkentin et al. .............. 607/23 |
| 2007/0199385 | A1 | 8/2007 | O'Brien et al. |
| 2007/0251338 | A1 | 11/2007 | Wiese et al. |
| 2007/0261497 | A1 | 11/2007 | O'Brien et al. |
| 2007/0269921 | A1 | 11/2007 | You |
| 2008/0027332 | A1 | 1/2008 | Bradley |
| 2008/0312726 | A1 | 12/2008 | Frank et al. |
| 2009/0057868 | A1 | 3/2009 | Wang et al. |
| 2009/0270707 | A1 | 10/2009 | Alfoqaha et al. |
| 2009/0308169 | A1 | 12/2009 | Mothilal et al. |
| 2010/0314149 | A1 | 12/2010 | Gerrish et al. |
| 2010/0314726 | A1 | 12/2010 | Mueller et al. |
| 2010/0314733 | A1 | 12/2010 | Mueller et al. |
| 2010/0315110 | A1 | 12/2010 | Fenner et al. |

OTHER PUBLICATIONS

U.S. Appl. No. 61/185,881, filed Jun. 10, 2009, Mueller et al.
U.S. Appl. No. 61/229,867, filed Jul. 30, 2009, Mueller et al.
U.S. Appl. No. 61/229,869, filed Jul. 30, 2009, Larson et al.
U.S. Appl. No. 61/235,745, filed Aug. 21, 2009, Gerrish et al.
U.S. Appl. No. 61/406,961, filed Oct. 26, 2010, O'Brien et al.
U.S. Appl. No. 13/016,363, filed Jan. 28, 2011, Mattes et al.
U.S. Appl. No. 13/302,725, filed Nov. 22, 2011, Mueller et al.
Lau, "MEMS Structures for Stress Measurements for Thin Films Deposited Using CVD," Master of Science Thesis, Massachusetts Institute of Technology, Feb. 2001, 79 pgs.
Lea et al., "DRIE from MEMS to wafer-level packaging," *Solid State Technology*, Dec. 2007; 50(12), 8 pgs. Retrieved online on Oct. 11, 2010. Available online at <url:http://www.electroiq.com/ElectroIQ/en-us/index/display/Semiconductor_Article_Tools_Template.articles.solid-state-technology.volume-50.issue-12.features.mems.drie-from-mems-to-wafer-level-packaging.html>.
Oberg et al., Machinery's Handbook, 25$^{th}$ edition, Industrial Press, New York, NY, 1996; title page, copyright page and p. 267. 2 pages total.
Osterberg et al., "M-TEST: A Test Chip for MEMS Using Electrostatically Actuated Test Structures" *Journal of Microelectromechanical Systems*, Jun. 1997; 6(2): 107-118.
Pham et al., "High-aspect-ratio bulk micromachined vias contacts," ProcSAFE & Prorisc 2004, Veldhoven, NL, Nov. 25-26, 2004, pp. 742-746.
Potkay, Joseph A., "Long term, implantable blood pressure monitoring systems," Biomed Microdevices (2008) 10:379-392; Published online: Dec. 20, 2007; © Springer Science + Business Media, LLC 2007.
Pham et al., "High-aspect-ratio bulk micromachined vias contacts," ProcSAFE & Prorisc 2004, Veldhoven, NL, Nov. 25-26, 2004, pp. 742-746.

\* cited by examiner

MEDICAL DEVICE ENCAPSULATED WITHIN BONDED DIES

FIELD

The present disclosure relates to a medical device and, in particular, a medical device encapsulated within bonded dies.

INTRODUCTION

Certain medical systems are designed to be implanted within a patient's body, such as implantable pulse generators (IPGs) and implantable cardioverter defibrillators (IPDs). In some cases, these implantable systems include certain medical device assemblies, such as sensors for detecting the patient's blood pressure or other patient characteristics. These characteristics can be measured in order to monitor the patient's anatomical functions, to monitor the performance of the system, and the like.

Medical device assemblies of this type are typically small so that they can be implanted within the patient. For instance, the assembly can be formed on a die substrate through etching, welding, and other methods of IC circuit manufacturing. Then, the die substrate is encased and hermetically sealed within a biocompatible case, such as a titanium case.

The present teachings provide various medical systems that relatively compact. Furthermore, the present teachings provide various techniques for manufacturing these types of medical devices efficiently.

SUMMARY

This section provides a general summary of the disclosure, and is not a comprehensive disclosure of its full scope or all of its features.

Various embodiments of an implantable medical system according to the present teachings are disclosed. An implantable medical system includes a first die substrate with a first outer surface. The system also includes a second die substrate with a second outer surface. Furthermore, the system includes a medical device with a first portion that is mounted to the first die substrate and a second portion that is mounted to the second die substrate. The first and second die substrates are fixed to each other and substantially hermetically sealed to each other. Also, the medical device is substantially encapsulated between the first and second die substrates. The first portion is electrically connected to the second portion. Moreover, the first and second outer surfaces of the first and second die substrates are directly exposed to a biological material.

The present teachings also provide a method of using a medical system. The method includes forming a first portion of a medical device on a first die substrate. The first die substrate has a first outer surface. Furthermore, the method includes forming a second portion of the medical device on a second die substrate. The second die substrate has a second outer surface. Additionally, the method includes fixing the first die substrate to the second die substrate to substantially hermetically seal the first die substrate to the second die substrate, to electrically connect the first and second portions of the medical device together, and to encapsulate the medical device therebetween. Moreover, the method includes implanting the medical system within a patient to directly expose the first and second outer surfaces to a biological material. The first and second die substrates act as a barrier between the biological material and the medical device.

In various embodiments, the present teachings further provide an implantable medical system that includes a cardiac device, a lead, and a medical device assembly. The medical device assembly includes a first die substrate with a first outer surface and a first mating surface. The first outer surface has an outer recess, and the first mating surface has an inner recess. Moreover, the medical device assembly includes a second die substrate with a second outer surface and a second mating surface. Furthermore, the medical device assembly includes a medical device with a first portion that is mounted to the first die substrate and a second portion that is mounted to the second die substrate. The first portion includes an outer electrode that is disposed within the outer recess and that is electrically connected to the lead. The first and second mating surfaces are directly bonded to each other non-adhesively to substantially hermetically seal the inner recess and to define a cavity therebetween. The first and second portions are electrically connected to each other, and the first and second die substrates encapsulate the medical device therebetween. The first portion includes a first pressure electrode that is disposed on an inner surface of the cavity on the first die substrate, and the second portion includes a second pressure electrode that is disposed on an inner surface of the cavity on the second die substrate. At least one of the first and second die substrates includes a diaphragm. The first and second pressure sensor electrodes cooperate to detect an amount of deflection of the diaphragm to detect a blood pressure and to send a corresponding signal to the cardiac device via the lead. The first and second outer surfaces of the first and second die substrates are directly exposed to blood and act as a barrier between the blood and the medical device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected exemplary embodiments and not all possible implementations, and are not intended to limit the scope of the present disclosure.

Corresponding reference numerals indicate corresponding parts throughout the several views of the drawings.

DETAILED DESCRIPTION

Exemplary embodiments will now be described more fully with reference to the accompanying drawings.

Figure 1:
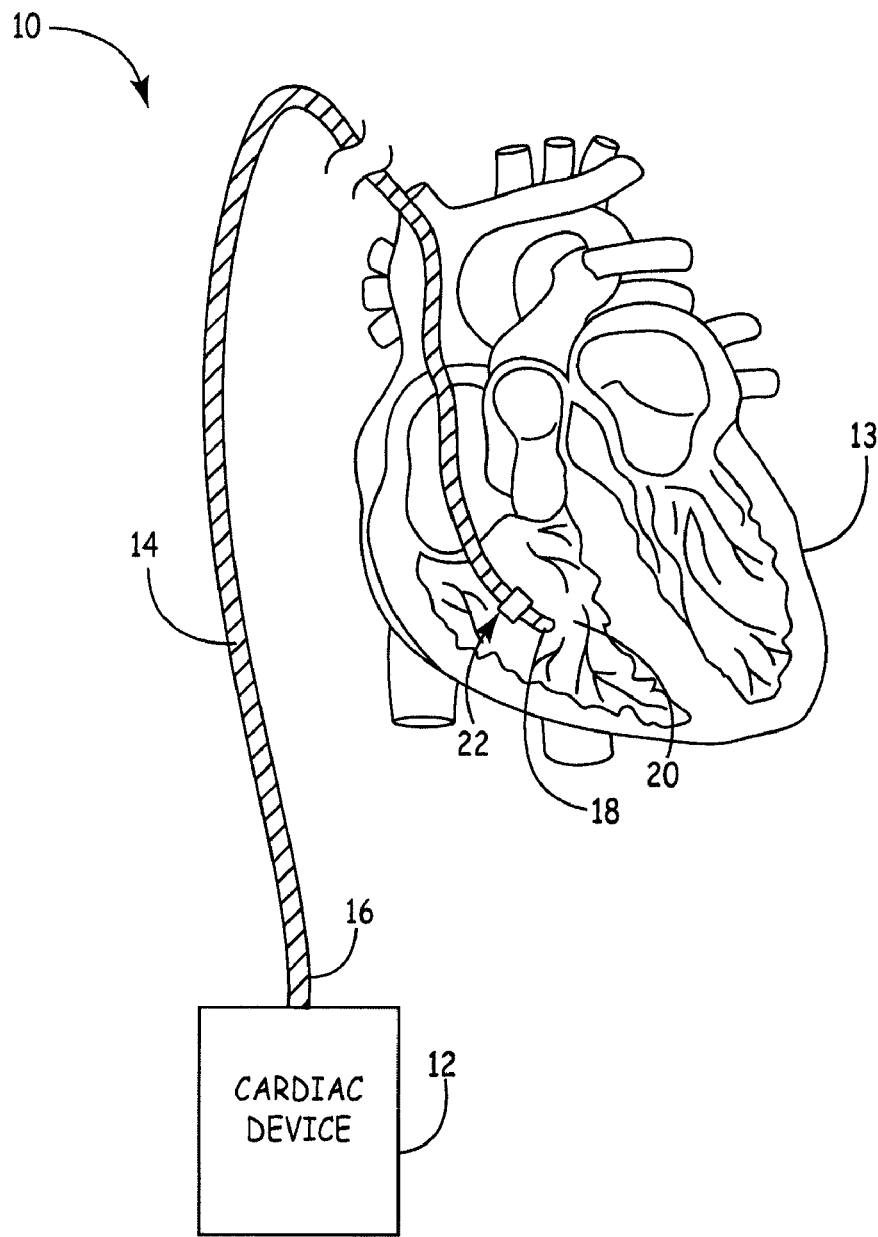
FIG. 1 is a schematic view of an implantable medical system with a medical device assembly according to various embodiments of the present teachings.

Referring initially to FIG. 1, an implantable medical system 10 is illustrated according to various exemplary embodiments of the present disclosure. Generally, the system 10 can include a cardiac device 12 and a lead 14. The cardiac device 12 can be of any suitable type for maintaining proper function of a heart 13 of a patient. For instance, the cardiac device 12 can be a pacemaker (IPG) for generating a pacing signal for the heart 13. The cardiac device 12 can also be a defibrillator (ICD) for generating a defibrillator signal for the heart 13. It will be appreciated that the cardiac device 12 can be implantable within the patient.

The lead 14 can be elongate and flexible. Also, the lead 14 can include an electrically conductive material, such as a metallic wire, that is coated with an electrically insulating material. Furthermore, the lead 14 can include a first end 16 that is electrically and mechanically connected to the cardiac device 12. In addition, the lead 14 can include a second end 18 that is electrically and mechanically connected to cardiac tissue 20 of the heart 13. As such, the lead 14 can transmit electrical signals (e.g., pacing signals, defibrillation signals, etc.) between the cardiac device 12 and the cardiac tissue 20 to maintain proper function of the heart 13.

In addition, the implantable medical system 10 can include a medical device assembly 22. The medical device assembly 22 can be operably coupled to the lead 14. For instance, the medical device assembly 22 can be operably mounted and electrically connected to the lead 14 adjacent the second end 18 of the lead 14.

As will be discussed, the medical device assembly 22 can operate in association with the cardiac device 12. In some exemplary embodiments, the medical device assembly 22 can be a microelectromechanical system (MEMS) of any suitable type. Accordingly, the medical device assembly 22 can be very small. In some exemplary embodiments, the medical device assembly 22 can be a pressure sensor for detecting blood pressure of the patient, as will be described in greater detail below. The medical device assembly 22 can, in turn, provide a feedback signal to the cardiac device 12, and the pacing, defibrillation, or other signal generated by the cardiac device 12 can be dependent on the feedback signal from the medical device assembly 22. However, it will be appreciated that the medical device assembly 22 can be adapted to detect any other suitable characteristic of any other suitable biological material. For instance, the medical device assembly 22 can, in some exemplary embodiments, detect the concentration of a certain chemical within the patient. Also, it will be appreciated that the medical device assembly 22 can be of any other suitable medical device other than a pressure sensor. For instance, the medical device assembly 22 can include a miniaturized gear system, a relay, a gyroscope, and the like.

Figure 2:
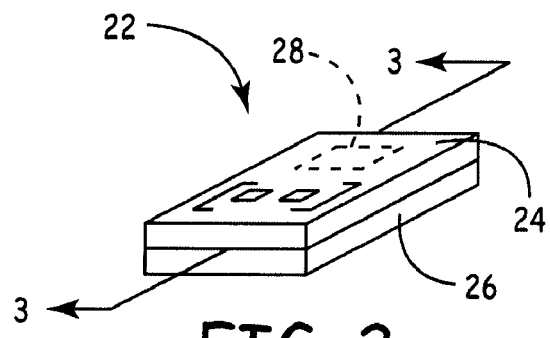
FIG. 2 is an isometric view of the medical device assembly of FIG. 1.
Figure 3:
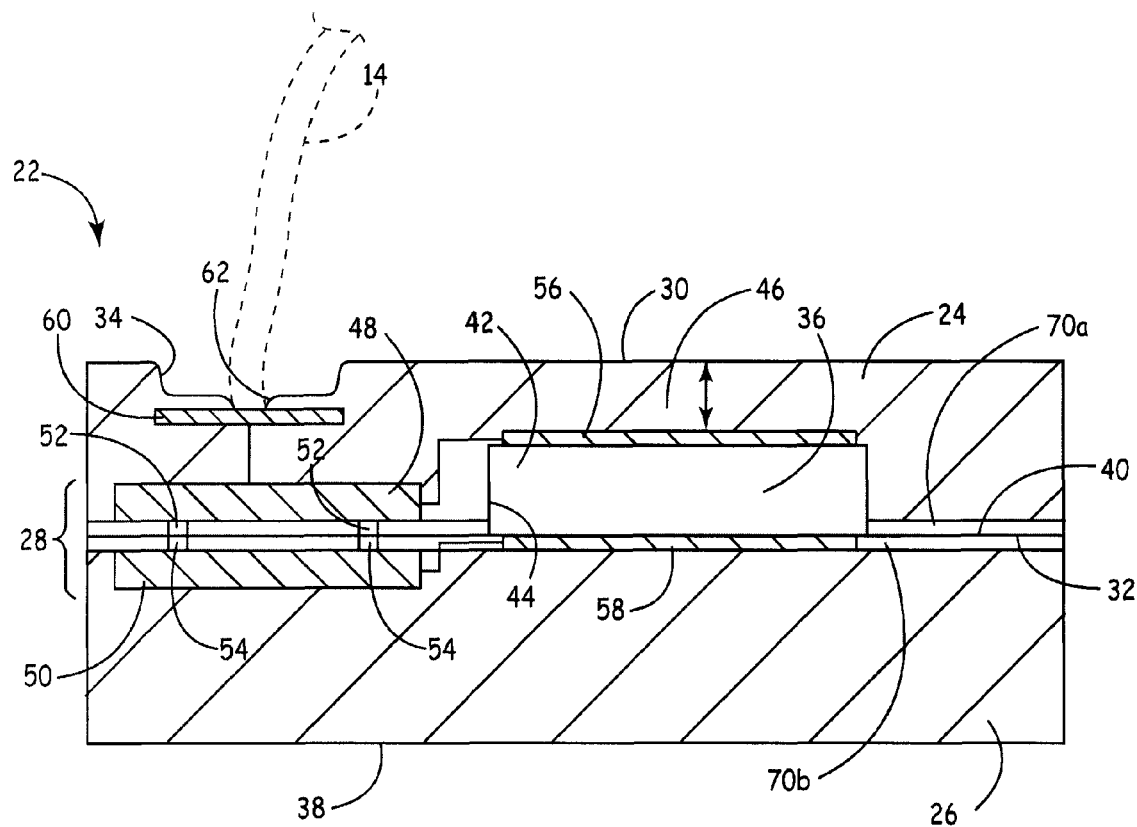
FIG. 3 is a schematic section view of the medical device assembly of FIG. 1.

Referring now to FIGS. 2 and 3, the medical device assembly 22 is illustrated in greater detail. As shown, the medical device assembly 22 can include a first die substrate 24, a second die substrate 26, and a medical device 28. For purposes of discussion, the medical device 28 will be described as a blood pressure sensor; however, the medical device 28 can be of any other suitable type.

The medical device 28 is encapsulated substantially within and between the first and second die substrates 24, 26. Also, the medical device 28 can be substantially and hermetically sealed within and between the first and second die substrates 24, 26. Moreover, as will be discussed in greater detail, the first and second die substrates 24, 26 can be directly exposed to the blood of the patient and act as a barrier between the blood and the medical device 28. As such, the medical device 28 can be protected substantially against contamination, and yet the medical device assembly 22 can be substantially compact.

The first and second die substrates 24, 26 are shown in greater detail in FIG. 3. As shown, the first die substrate 24 can include an outer surface 30 and a mating surface 32 for mating with the second die substrate 26. Also, the outer surface 30 can include an outer recess 34, and the mating surface 32 can include an inner recess 36. Furthermore, the second die substrate 26 can include an outer surface 38 and a mating surface 40 for mating with the first die substrate 24. It will be appreciated that the first and second die substrates 24, 26 can be made out of any suitable material, such as silicon, glass, or another suitable bio-compatible material. Furthermore, as will be discussed, the first and second die substrates 24, 26 can be cut from a larger wafer, such as a silicon wafer.

Moreover, as shown in FIG. 3, the mating surface 32 of the first die substrate 24 can be fixedly mated to the mating surface 40 of the second die substrate 26. As will be discussed, the mating surfaces 32, 40 can be directly bonded without the use of adhesives (i.e., non-adhesively).

Furthermore, when mated, the first and second die substrates 24, 26 cooperate to define a cavity 42 therebetween. More specifically, the cavity 42 is defined by an inner surface 44 of the inner recess 36 and the second mating surface 40 of the second die substrate 26. As such, the cavity 42 is enclosed and substantially hermetically sealed between the first and second die substrates 24, 26. It will be appreciated that the cavity 42 can substantially house and encapsulate at least a portion of the medical device 28.

Furthermore, the first die substrate 24 can include a diaphragm 46. More specifically, the first die substrate 24 can be relatively thin adjacent the cavity 42 to thereby define the diaphragm 46. Because it is thin, the diaphragm 46 can deflect, as will be discussed, to thereby change the volume of the cavity 42. For example, blood pressure can cause the diaphragm 46 to deflect, and the medical device 28 can detect an amount of deflection to detect the blood pressure, as will be discussed.

Additionally, the medical device 28 can include a first portion 48 mounted to the first die substrate 24 and a second portion 50 mounted to the second die substrate 26. The first and second portions 48, 50 can each include various electrical components, such as a microprocessor, a transistor, a capacitor, a diode, a resistor, vias, electrical traces, and the like. Furthermore, the first and second portions 48, 50 can be embedded at least partially within the respective die substrates 24, 26. Also, the medical device 28 can include a plurality of first plugs 52 and a plurality of second plugs 54. The first plugs 52 can be exposed on the first mating surface 32, and the second plugs 54 can extend out and be exposed from the second mating surface 40. Each of the first plugs 52 can be electrically connected to corresponding ones of the second plugs 54 when the first and second die substrates 24, 26 are fixed together. As such, the first and second portions 48, 50 of the medical device 28 can be in electrical communication with each other so that the medical device 28 can function.

Furthermore, the first portion 48 of the medical device 28 can include a first sensor electrode 56. The first sensor electrode 56 can be disposed adjacent (e.g., fixed to) the inner surface 44 of the cavity 42 on the first die substrate 24. Moreover, the second portion 50 of the medical device 28 can include a second sensor electrode 58. The second sensor electrode 58 can be disposed adjacent (e.g., fixed to) the inner surface 44 of the cavity 42 on the second die substrate 26. The first and second electrodes 56, 58 can be disposed opposite from each other and spaced apart in the cavity 42. Thus, as the diaphragm 46 deflects, the first and second sensor electrodes 56, 58 can move relative to each other. By applying a voltage between the electrodes 56, 58 and monitoring voltage changes between the electrodes 56, 58, the medical device 28 can detect a change in capacitance or other characteristic due to the relative movement of the electrodes 56, 58. As such, the medical device 28 can detect the blood pressure of the patient.

Additionally, the first portion 48 of the medical device 28 can include an outer electrode 60. The outer electrode 60 can be disposed adjacent the outer recess 34 of the first die substrate 24. The outer electrode 60 can be exposed from the first die substrate 24 by an opening 62 in the outer surface 30 of the first die substrate 24. Furthermore, the lead 14 of the system 10 can be electrically connected to the outer electrode 60, as shown in phantom in FIG. 3. As such, the outer electrode 60 can allow electrical signals to be transmitted between the lead 14 and the medical device 28.

Figure 5:
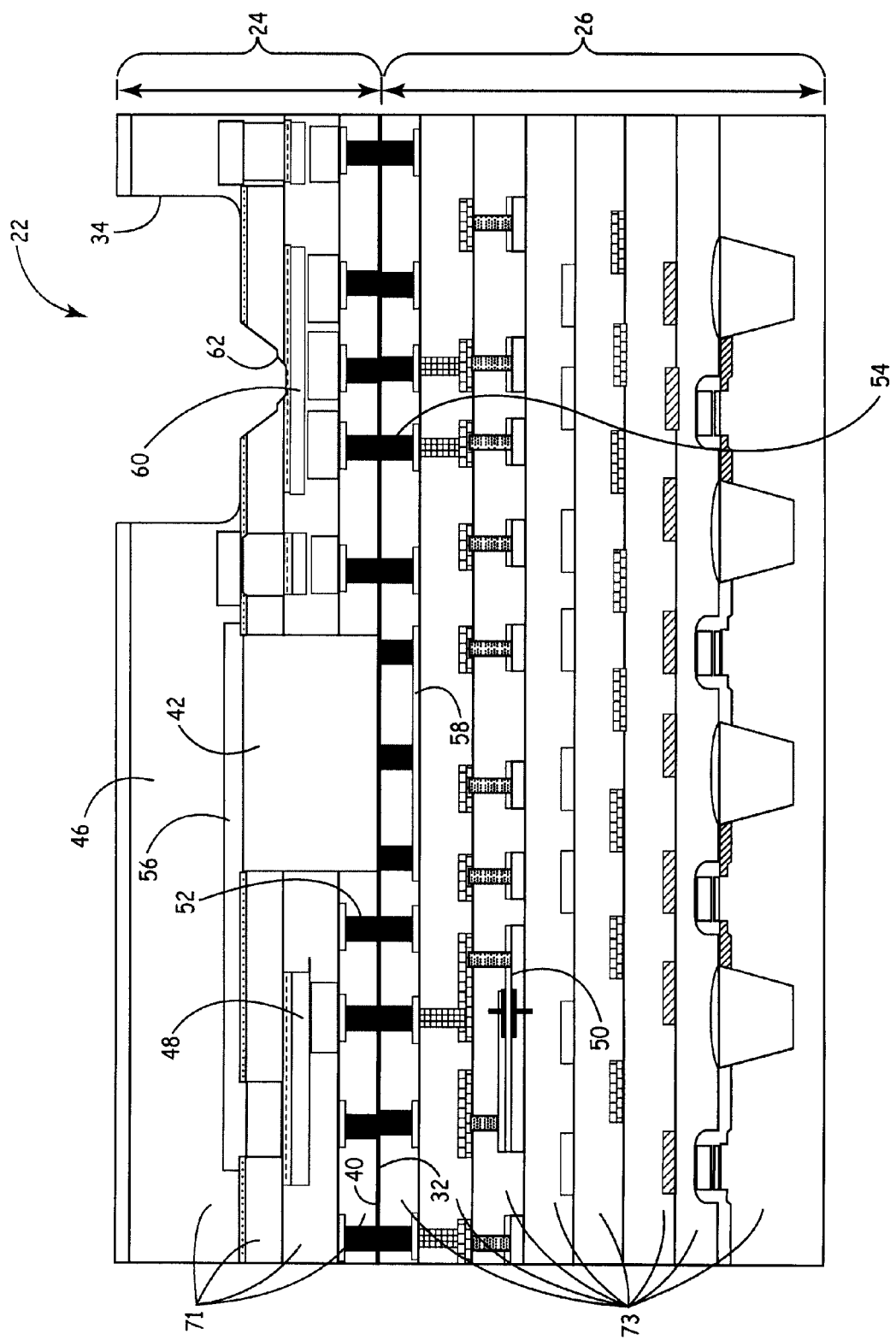
FIG. 5 is a schematic section view of the medical device assembly according to another exemplary embodiment.

Referring now to FIG. 5, an exemplary embodiment of the medical device assembly 22 is shown in greater detail. As shown, the first die substrate 24 can include a plurality of layers 71 that are disposed on top of each other, and the second die substrate 26 can similarly include a plurality of layers 73 that are disposed on top of each other. The first and second portions 48, 50 of the medical device 28 can be layered on, embedded within, and extend through the individual layers 71, 73. As will be discussed, the medical device 28 can be manufactured according to various known semiconductor manufacturing methods.

Accordingly, the medical device assembly 22 can be implanted within a patient. The first and second die substrates 24, 26 can be directly exposed to biological materials, such as blood. The first and second die substrates 24, 26 can act as a barrier between the blood and the medical device 28 to thereby reduce the likelihood of contamination of the medical device 28. As such, the medical device assembly 22 can be very compact, and yet the medical device assembly 22 can still function accurately over a long period of time without contamination.

Figure 4A:
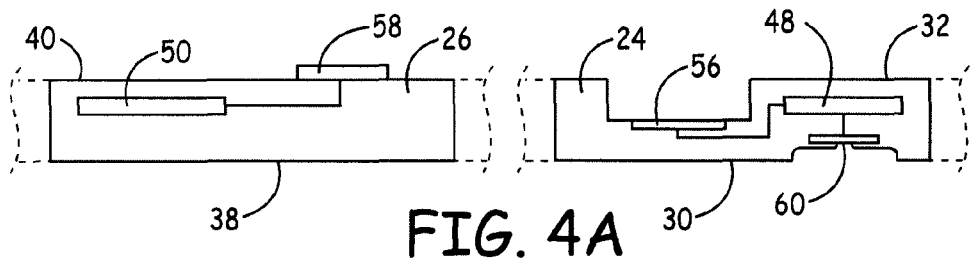
FIGS. 4A-4D are schematic section views illustrating a method of manufacturing the medical device assembly of FIG. 1.

Referring now to FIGS. 4A-4D, a method of manufacturing the medical device assembly 22 is illustrated. As shown in FIG. 4A, the first portion 48 of the medical device 28 can be formed on the first die substrate 24. Likewise, the second portion 50 of the medical device 28 can be formed on the second die substrate 26. The first and second portions 48, 50 can be formed using any suitable semiconductor manufacturing technique, such as deposition, removal, patterning, modification (doping), front end processing, etc. Also, the first and second portions 48, 50 can be formed when the first and second substrates 24, 26 are part of a larger wafer, as represented in phantom lines in FIG. 4A.

Figure 4B:
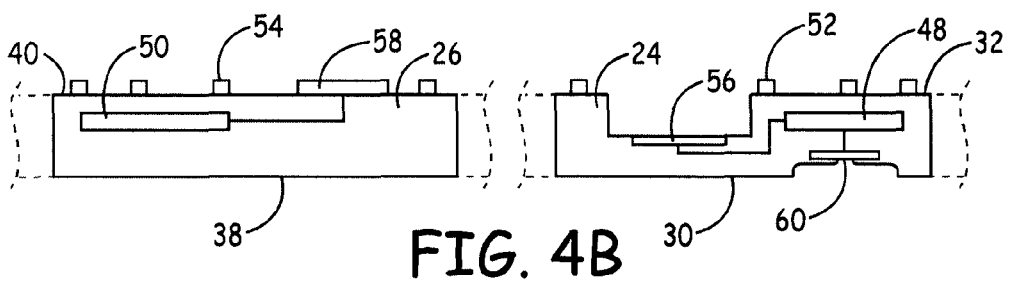

Then, as shown in FIG. 4B, the plugs 52, 54 can be formed. For instance, a layer of metal or other electrically conductive material can be sputtered on the respective mating surfaces 32, 40 of the first and second die substrates 24, 26. Then, a photoresist mask (not shown) can be applied, and the plugs 52, 54 can be patterned. Subsequently, the photoresist can be removed.

Figure 4C:
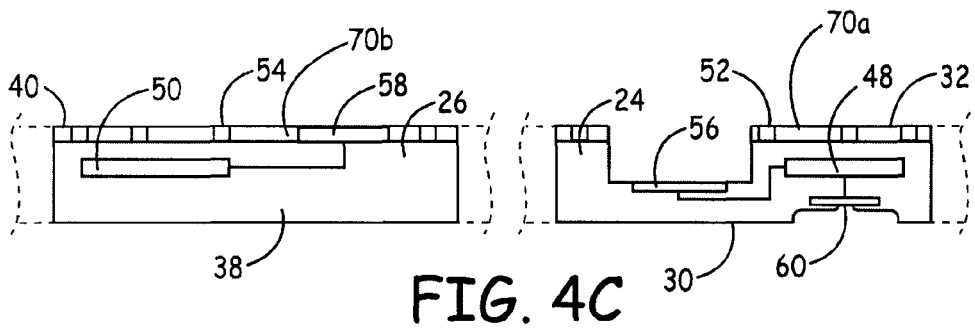

Next, as shown in FIG. 4C, a glass layer 70*a*, 70*b* can be applied to the respective mating surfaces 32, 40 of the first and second die substrates 24, 26. The mating surfaces 32, 40 can then be polished to smooth the mating surfaces 32, 40 and to expose the plugs 52, 54.

Figure 4D:
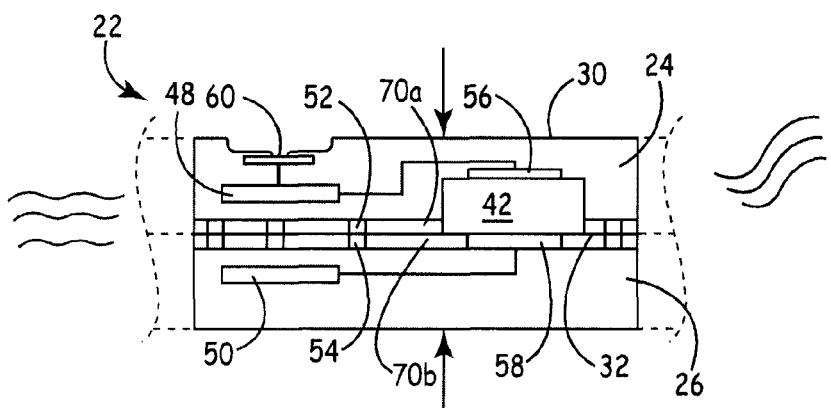

Subsequently, as shown in FIG. 4D, the first and second die substrates 24, 26 can be mated by pushing the mating surfaces 32, 40 together (as represented by vertical arrows in FIG. 4D) and applying heat (e.g., 100-200° F.). Once cooled, the plugs 52, 54 can expand into each other and bond together, and the glass layers 70*a*, 70*b* can do the same. Accordingly, the first and second portions 48, 50 of the medical device 28 can be in electrical communication, and the first and second die substrates 24, 26 can be bonded and substantially hermetically sealed together.

As such, the medical device assembly 22 can be relative easily to manufacture. Also, the medical device assembly 22 can include fewer parts such that materials costs and other manufacturing costs are reduced. Additionally, as mentioned above, the medical device assembly 22 can be relatively compact.

The foregoing description of the exemplary embodiments has been provided for purposes of illustration and description. It is not intended to be exhaustive or to limit the invention. Individual elements or features of a particular exemplary embodiment are generally not limited to that particular exemplary embodiment, but, where applicable, are interchangeable and can be used in a selected exemplary embodiment, even if not specifically shown or described. The same may also be varied in many ways. Such variations are not to be regarded as a departure from the invention, and all such modifications are intended to be included within the scope of the invention.

Exemplary embodiments are provided so that this disclosure will be thorough, and will fully convey the scope to those who are skilled in the art. Numerous specific details are set forth such as examples of specific components, devices, and methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. An implantable medical system comprising:
    a first die substrate with a first outer surface;
    a second die substrate with a second outer surface; and
    a medical device with a first portion that is mounted to the first die substrate and a second portion that is mounted to the second die substrate, wherein the first portion comprises at least one first conductive element terminating at a mating surface and the second portion comprises at least one second conductive element terminating at a mating surface, the first and second die substrates being fixed to each other and substantially hermetically sealed to each other, the medical device substantially encapsulated between the first and second die substrates, the at least one first conductive element of the first portion being electrically connected to the at least one second conductive element of the second portion when the first and second die substrates substantially hermetically seal and substantially encapsulate the medical device, the first and second outer surfaces of the first and second die substrates being directly exposed to a biological material.

2. The implantable medical system of claim 1, wherein the first and second die substrates cooperate to define a cavity that is enclosed and substantially hermetically sealed between the first and second die substrates.

3. The implantable medical system of claim 2, wherein the first die substrate includes a first mating surface with an inner recess, wherein the second die substrate includes a second mating surface, and wherein the first and second mating surfaces are fixed to each other to substantially hermetically seal the inner recess and to define the cavity.

4. The implantable medical system of claim 2, wherein the first portion of the medical device includes a first sensor electrode that is disposed on an interior surface of the cavity on the first die substrate, and wherein the second portion of the medical device includes a second sensor electrode that is disposed on an interior surface of the cavity on the second die substrate, the first and second sensor electrodes cooperating with each other to detect a characteristic of the biological material.

5. The implantable medical system of claim 4, wherein at least one of the first and second die substrates includes a diaphragm that is deflectable by the biological material to move at least one of the first and second sensor electrodes relative to the other.

6. The implantable medical system of claim 5, wherein the medical device is a pressure sensor that detects a pressure of the biological material based on deflection of the diaphragm by the biological material.

7. The implantable medical system of claim 1, wherein the first outer surface includes an outer recess, and further comprising an outer electrode disposed within the outer recess, the outer electrode in electrical communication with the medical device.

8. The implantable medical system of claim 1, wherein the first and second die substrates are bonded directly together non-adhesively.

9. The implantable medical system of claim 1, wherein the first and second die substrates each include a plurality of layers, and wherein the first portion and the second portion are each at least partially embedded within the respective plurality of layers.

10. The implantable medical system of claim 1, further comprising a cardiac device and a lead, the lead being coupled to the first and second die substrates and being in electrical communication with the medical device, the medical device in communication with the cardiac device via the lead.

11. A method of using a medical system comprising:
    forming a first portion of a medical device on a first die substrate, the first die substrate having a first outer surface, wherein the first portion comprises at least one first conductive element terminating at a mating surface;
    forming a second portion of the medical device on a second die substrate, the second die substrate having a second outer surface, wherein the second portion comprises at least one second conductive element terminating at a mating surface;
    fixing the first die substrate to the second die substrate to substantially hermetically seal the medical device between the first die substrate and the second die substrate, to electrically connect the at least one first conductive element of the first portion and the at least one second conductive element of the second portion of the medical device together, and to encapsulate the medical device therebetween; and
    implanting the medical system within a patient to directly expose the first and second outer surfaces to a biological material, the first and second die substrates acting as a barrier between the biological material and the medical device.

12. The method of claim 11, further comprising detecting a characteristic of the biological material with the medical device.

13. The method of claim 12, wherein detecting a characteristic of the biological material comprises detecting a pressure of the biological material.

14. The method of claim 11, wherein fixing the first die substrate to the second die substrate comprises defining a substantially hermetically sealed cavity between the first die substrate and the second die substrate.

15. The method of claim 14, wherein fixing the first die substrate to the second die substrate comprises mating a first mating surface of the first die substrate to a second mating surface of the second die substrate, the first mating surface including an inner recess, and wherein mating the first mating surface to the second mating surface comprises substantially hermetically sealing the inner recess to define the cavity.

16. The method of claim 14, further comprising disposing a first sensor electrode on an interior surface of the cavity on the first die substrate, and further comprising disposing a second sensor electrode on an interior surface of the cavity on the second die substrate, the first and second sensor electrodes cooperating with each other to detect a characteristic of the biological material.

17. The method of claim 16, wherein the method further comprises detecting a characteristic of the biological material, wherein detecting the characteristic of biological material comprises detecting an amount of deflection of a diaphragm included on at least one of the first and second die substrates based on a distance between the first and second sensor electrodes.

18. The method of claim 11, further comprising forming an outer recess on the first outer surface, disposing an outer electrode within the outer recess, and electrically connecting the outer electrode to the medical device.

19. The method of claim 11, wherein fixing the first die substrate to the second die substrate comprises bonding the first die substrate directly to the second die substrate non-adhesively.

20. The method of claim 19, further comprising applying at least one of heat and pressure to bond the first die substrate directly to the second die substrate.

21. The method of claim 11, wherein forming the first portion of the medical device on the first die substrate comprises embedding at least part of the first portion within a plurality of layers of the first die substrate, and wherein forming the second portion of the medical device on the second die substrate comprises embedding at least part of the second portion within a plurality of layers of the second die substrate.

22. The method of claim 11, further comprising implanting a cardiac device and a lead, the lead being coupled to the first and second die substrates and being in electrical communication with the medical device, and further comprising transmitting a signal between the medical device and the cardiac device via the lead.

23. An implantable medical system comprising:
a cardiac device;
a lead; and
a medical device assembly comprising:
a first die substrate with a first outer surface and a first mating surface, the first outer surface having an outer recess, and the first mating surface having an inner recess;
a second die substrate with a second outer surface and a second mating surface; and
a medical device with a first portion that is mounted to the first die substrate and a second portion that is mounted to the second die substrate, wherein the first portion comprises at least one first conductive element terminating at the first mating surface and the second portion comprises at least one second conductive element terminating at the second mating surface, the first portion including an outer electrode that is disposed within the outer recess and that is electrically connected to the lead, the first and second mating surfaces being directly bonded to each other non-adhesively to substantially hermetically seal the inner recess and to define a cavity therebetween, the at least one first conductive element of the first portion and the at least one second conductive element of the second portions being electrically connected to each other, the first and second die substrates encapsulating the medical device therebetween, the first portion including a first pressure electrode that is disposed on an inner surface of the cavity on the first die substrate, the second portion including a second pressure electrode that is disposed on an inner surface of the cavity on the second die substrate, at least one of the first and second die substrates including a diaphragm, the first and second pressure sensor electrodes cooperating to detect an amount of deflection of the diaphragm to detect a blood pressure and sending a corresponding signal to the cardiac device via the lead, the first and second outer surfaces of the first and second die substrates being directly exposed to blood and acting as a barrier between the blood and the medical device.

\* \* \* \* \*

UNITED STATES PATENT AND TRADEMARK OFFICE
CERTIFICATE OF CORRECTION

| | |
|---|---|
| PATENT NO. | : 8,172,760 B2 |
| APPLICATION NO. | : 12/487369 |
| DATED | : May 8, 2012 |
| INVENTOR(S) | : Michael F. Mattes |

It is certified that error appears in the above-identified patent and that said Letters Patent is hereby corrected as shown below:

Col. 10, line 21, delete "of the second portions" and insert in place thereof --of the second portion--;

Signed and Sealed this
Thirtieth Day of October, 2012

David J. Kappos
*Director of the United States Patent and Trademark Office*